United States Patent [19]

Jaeggi

[11] Patent Number: 5,522,265
[45] Date of Patent: Jun. 4, 1996

[54] DEVICE FOR THE ULTRASONIC MEASURING OF THE DEFECTS OF A RAILWAY TRACK

[75] Inventor: J. P. Jaeggi, Geneva, Switzerland

[73] Assignee: Speno International SA, Geneva, Switzerland

[21] Appl. No.: 404,265

[22] Filed: Mar. 14, 1995

[30] Foreign Application Priority Data

Apr. 6, 1994 [CH] Switzerland ............... 1003/94
Dec. 20, 1994 [CH] Switzerland ............... 3843/94

[51] Int. Cl.$^6$ ............... G01N 29/10; G01N 29/24; G01N 29/26
[52] U.S. Cl. ............... 73/625; 73/628; 73/634; 73/636; 73/431; 73/866.5
[58] Field of Search ............... 73/866.5, 620, 73/625, 628, 634, 636, 641, 493, 431

[56] References Cited

U.S. PATENT DOCUMENTS

| | | | |
|---|---|---|---|
| 3,028,751 | 4/1962 | Joy | 73/634 |
| 3,028,753 | 4/1962 | Joy | 73/636 |
| 3,251,220 | 5/1966 | Joy | 73/636 |
| 3,279,242 | 10/1966 | Megoloff | 73/644 |
| 3,960,005 | 6/1976 | Vezina | 73/614 |
| 3,962,908 | 6/1976 | Joy | 73/636 |
| 4,044,594 | 8/1977 | Owens et al. | 73/636 |
| 4,468,966 | 9/1984 | Bradshaw . | |
| 4,662,224 | 5/1987 | Turbe . | |
| 4,700,574 | 10/1987 | Turbe . | |

FOREIGN PATENT DOCUMENTS 0160591 11/1985 European Pat. Off. .
0164168 12/1985 European Pat. Off. .

*Primary Examiner*—Hezron E. Williams
*Assistant Examiner*—Rose M. Finley
*Attorney, Agent, or Firm*—Young & Thompson

[57] ABSTRACT

A shoe (1) is provided which includes two housings designed for receiving ultrasonic probes (2) of which the vertical position with respect to the track is adjustable via two pressure cylinders (9). The shoe (1) is connected via two pressure cylinders (13) to a frame (12, 22, 23) designed for mounting under a railway vehicle. The shoe (1) is guided and driven along the track by deformable rings (14). Conduits (15, 16) are arranged in the body of the shoe (1) in such a manner as to allow the supply of a fluid in front of the probes (2) and the recovery of one part of this fluid behind said probes (2). Cleaning shoes (30, 30') and high pressure sprayers (31, 31') clean the track in front of the measuring carriage.

15 Claims, 5 Drawing Sheets

FIG. 5
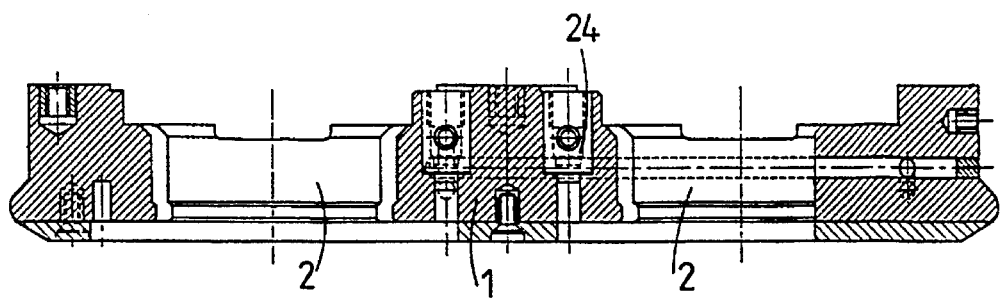
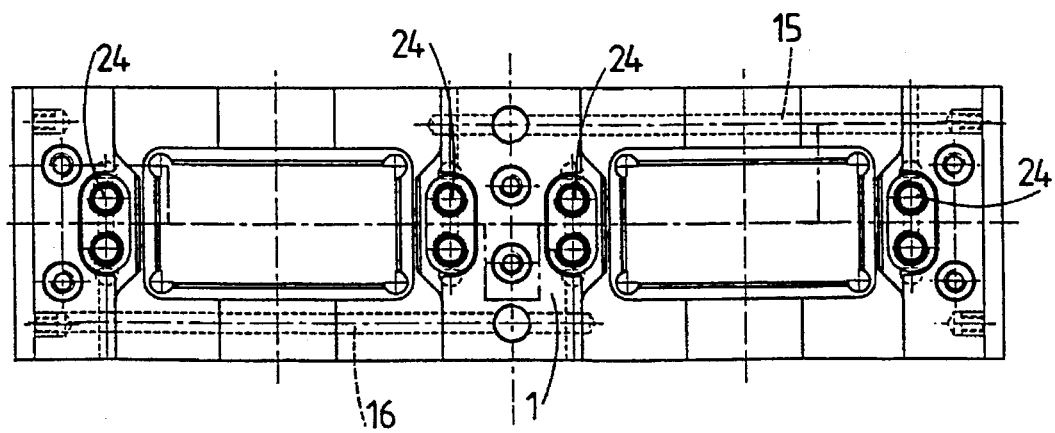
FIG. 6

DEVICE FOR THE ULTRASONIC MEASURING OF THE DEFECTS OF A RAILWAY TRACK

The present invention is concerned with a device for measuring the internal defects of a track of a railway and, more particularly, an ultrasonic device designed for working on the railway. Devices which make it possible to analyse a body by a beam of ultrasounds are well known and they are used for the measure of internal defects of the tracks of a railway both in the field and in a workshop. According to this principle, a beam of ultrasounds is emitted in the direction of the track from a probe placed on the upper face of the track, the energy is reflected by the track and its defects are then detected and measured by appropriate electronic circuits. The U.S. Pat. Nos. 4,662,224 and 4,700,574 teach measuring methods as well as devices for their implementation. It is essential for obtaining a measure which is reliable of all the defects of the track, to ensure the best acoustical contact possible between the probe and the track.

The geometric position of the track is never perfect, and defective alignment, punctual deformations or the discontinuities of the track cause the probes to jump on the track and therefore to loose the acoustic connection, which accordingly disturbs the measuring. These perturbations are all the more important as the speed of the operation is higher. Railway installations such as points for example are important discontinuities which subject the probes to high forces which can tear them off upon passage of the measuring vehicle.

The existing carriages for verifying railway tracks include a dozen probes per track, to ensure a complete verification of all the defects of the track. These probes are generally, carried by a common beam driven and guided along the track by adequate means. Considering the necessary length of this support beam, its mass and the number of probes carried, it is extremely, difficult to guarantee constantly a perfect probe—track contact for all the probes and accordingly, these devices are not adapted to the verification of tracks at high speed.

The purpose of the present invention is to obviate the above-mentioned defects. The applicant proposes to this end a device for measuring by ultrasounds designed to be mounted beneath a railway vehicle which guarantees a perfect acoustic contact between each probe and the track. This device makes it also possible to avoid that the probes be damaged upon passage over important discontinuities of the tracks. It is thus possible, with the device object of this invention, to carry out reliable measurements of all the internal defects of the track at high speeds, in the order of 100 km/h.

The annexed drawing illustrate schematically and by way of example an embodiment of the measuring device according to the present invention.

FIG. 5 is a side view partly in cross-section of a second embodiment of the lower part of the measuring device.

FIG. 6 is a top view of the device illustrated in FIG. 5.

Figure 1:
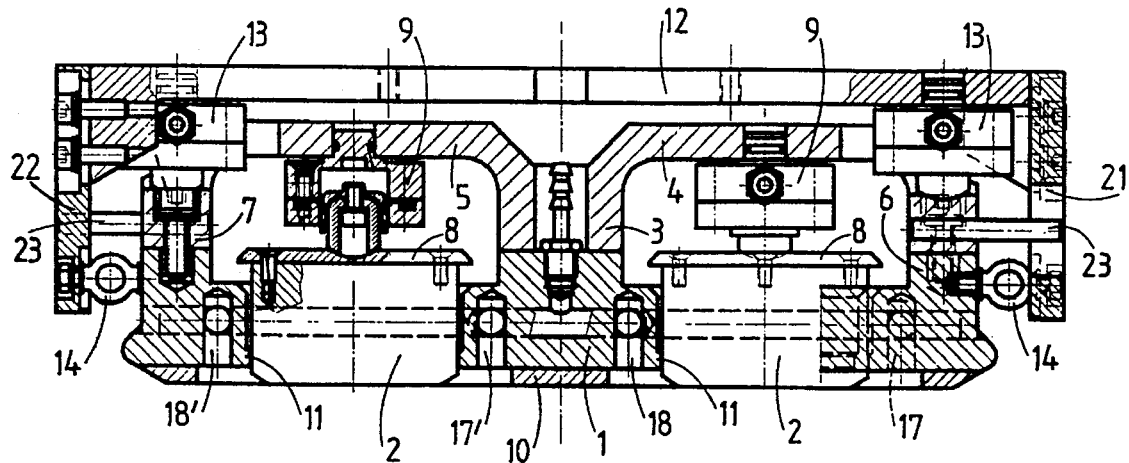
FIG. 1 is a lateral view partially in cross-section of the measuring device according to the present invention.

FIG. 1 illustrates a device foe measuring by ultrasounds which includes a shoe 1 including two housings in which can slide vertically the ultrasonic probes 2. The upper part of the shoe 1 includes a central post 3 provided with two side arms 4, 5 connecting respectively the front post 6 and the rear post 7 of the shoe 1. Each probe 2 is mounted under a support plate 8. These support plates 8 are connected to the side arms 4, 5 via adjustable pressure cylinders 9. These cylinders 9 make it possible to bias the probes 2 against the track with a determined force. The biasing pressure exerted by these cylinders 9 can be adapted to the speed of progression of the device. The higher the speed, the greater the pressure with which the probes will have to be applied against the track, to avoid that they bump off. Instead of the cylinders 9, one can provide calibrated springs. The vertical travel of the probes is limited downwards by the support plates 8 of which the dimensions are greater than those of the housings in which slide the probes 2. One thus avoids that a probe 2 falls out upon passage over an important discontinuity of the track, as the middle of a railway derivation for example. A bottom plate 10 provided with cutouts which correspond to the housings of the shoe i is fastened by screws (not illustrated) under the shoe 1. This shoe generally made of a plastic material makes it possible for the shoe to slide along the track with reduced friction and reduced wear. The housings in which slide the probes 2 exhibit in their lower part, immediately beneath the shoe 10, a small shoulder 11 which ensures a longitudinal and a transverse guiding of the probes with respect to the track.

The upper part of the shoe 1 is connected to a frame consisting of a support beam 12 upon which are fastened two lateral plates, one front plate 21 and one back plate 22. The vertical front post 6 and rear post 7 of the shoe 1 are connected by means of the two cylinders 13 to the support beam 12. These cylinders 13 make it possible to bias the bottom plate 10 of the shoe 1 against the track with a predetermined force and to lift the shoe when light running for example. Deformable rings made of rubber 14 connect the front vertical post 6 and the rear vertical post 7 of the shoe 1 respectively to the front plate 21 and the back plate 22 of the frame. These deformable rings 14 make it possible to drive the shoe in the direction of travel. These deformable rings 14 made of rubber make it also possible to dampen the vibrations of the probes 2 and of the shoe 1 as the device advances. These deformable rings can be replaced by any other elastic members, such as springs or silent blocs. Rods 23 mounted in the front posts 6 and 7 of the shoe 1 slide vertically in the housings made in the front plate 21 and the rear plate 22 of the frame. These housings are in the form of a vertical slot of which the width corresponds to the diameter of the rods 23. Accordingly, these rods 23 ensure both the lateral guiding of the shoe with respect to the frame and a limitation of the travel of the shoe downwards when it moves with respect to the frame under the action of the cylinders 13.

Figure 2:
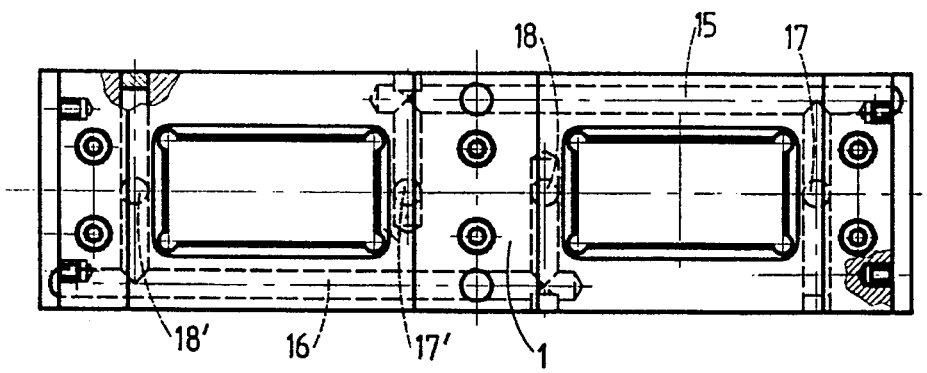
FIG. 2 is a partial top view of the device illustrated in FIG. 1.

The shoe 1 includes a water distribution conduit 15 and a water recovery circuit 16 situated in the body of the shoe 1 as illustrated in FIG. 2. The conduit 15 for supplying water opens via channels 17, 17' at the front of the probes 2 into a chamber formed by the cutout portion of the bottom plate 10. The conduit 16 for the recovery of the water opens via channels 18, 18' at the back of each probe 2 into a chamber formed by the cutout portion of the bottom plate 10. It is thus possible to bring the water channels 17, 17' into the chamber situated at the front of the probes, so that a water film is formed between the probe 2 and the track, guaranteeing thereby an excellent acoustical contact between the probe and the track.

Figure 3:
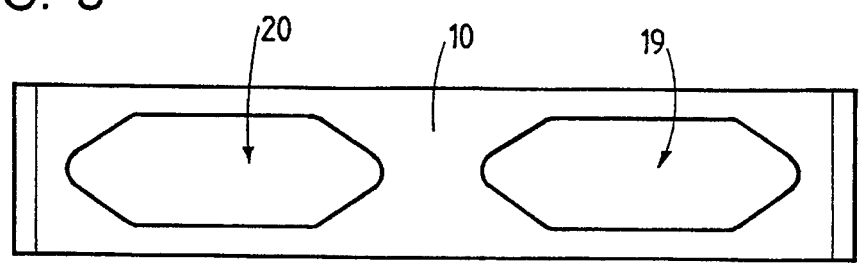
FIG. 3 is a top view of the bottom plate of the device according to FIG. 1.

FIG. 3 illustrates the shape of the cutouts provided in the bottom plate 10 and hence the shape of the chambers thus defined at the front and at the back of the probes. These cutouts 19, 20 reproduce the rectangular shape of the probes in their central part to allow the passage of the probe 2 and extend forwards and backwards as a cutout of a triangular shape. The triangular shape of these cutouts promotes the uniform distribution of water at the front of the probes and makes it possible to direct the water to be recovered towards the recovery channels 18, 18' at the back of the probes 2. Owing to this configuration, it is possible not only to guarantee a good acoustic contact between the probe and the track, but also to recover a considerable amount of water, which increases the travel range of the measuring device on the track. The symmetrical shape of the device and of the cutouts of the bottom plate make it possible to use the device when travelling forwards or backwards. One will in particular take care when changing the direction in which the device runs, to switch over the supply of the conduits 17, 17', 18, 18'.

Figure 4:
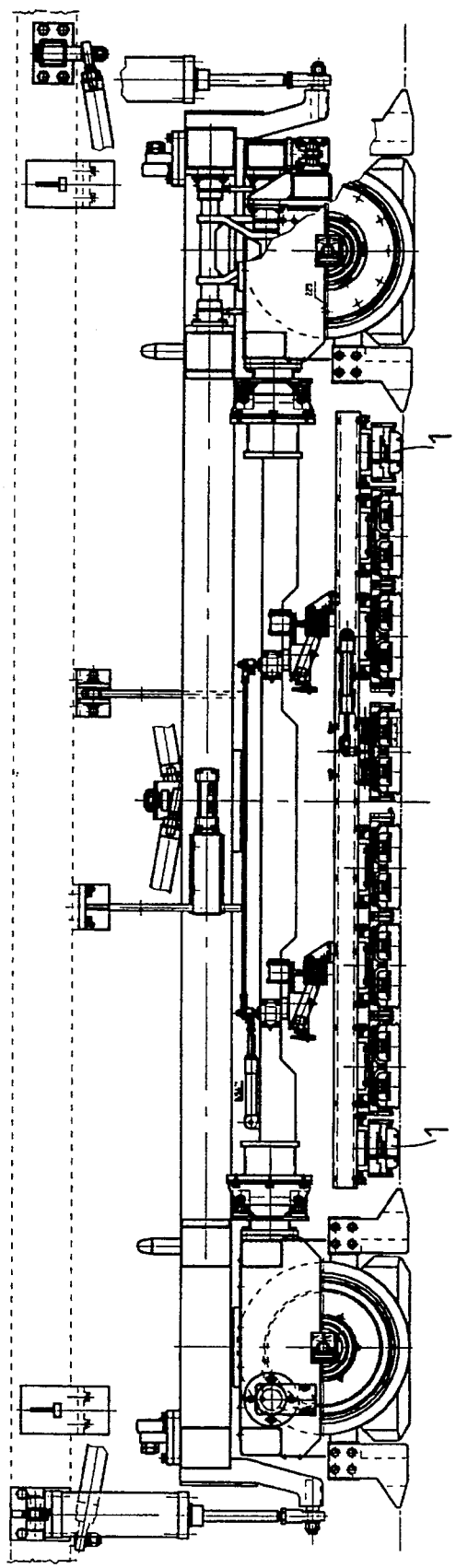
FIG. 4 is a side view of several measuring devices according to the present invention mounted under a railway vehicle.

FIG. 4 is a side view illustrating a carriage for verifying railway tracks mounted beneath a railway vehicle and including several measuring units, object of the present invention.

For the purpose on the one hand of sparing the water necessary to the functioning of the measuring installation and of increasing in a corresponding manner the travelling range and, on the other hand, to improve the contact between the probe and the rail, a second embodiment of the measuring device carrying probes was proposed. This second embodiment will be described with reference to FIGS. 5 and 6. The water supply conduits 15 and the water recovery conduit 16 supply the spray nozzles 24. These nozzles 24 have a diameter of about 0.4 mm and operate under a pressure comprised between 10 and 15 bars. They make possible the formation of a cone of finely sprayed water. This water cone thus formed has an opening of about 35° and the distance between the base of the cone and the opening of the nozzle 24 is about 15 mm. Owing to the dimensions and the orientation of these nozzles 24, it is possible to form the water film required for the optimal probe—rail contact. Actually, the periphery of the base of the water cone formed by these nozzles 24 is directly in contact with the track and promotes the formation of a film of water which is uniform on the rail head. The adjustment of the flow of the nozzles 24 can be controlled by the speed of travel of the device, which makes possible the formation of an optimal water film. It is thus possible to deduce even further the water consumption by comparison with the first embodiment illustrated in FIGS. 1 to 3.

Figure 7:
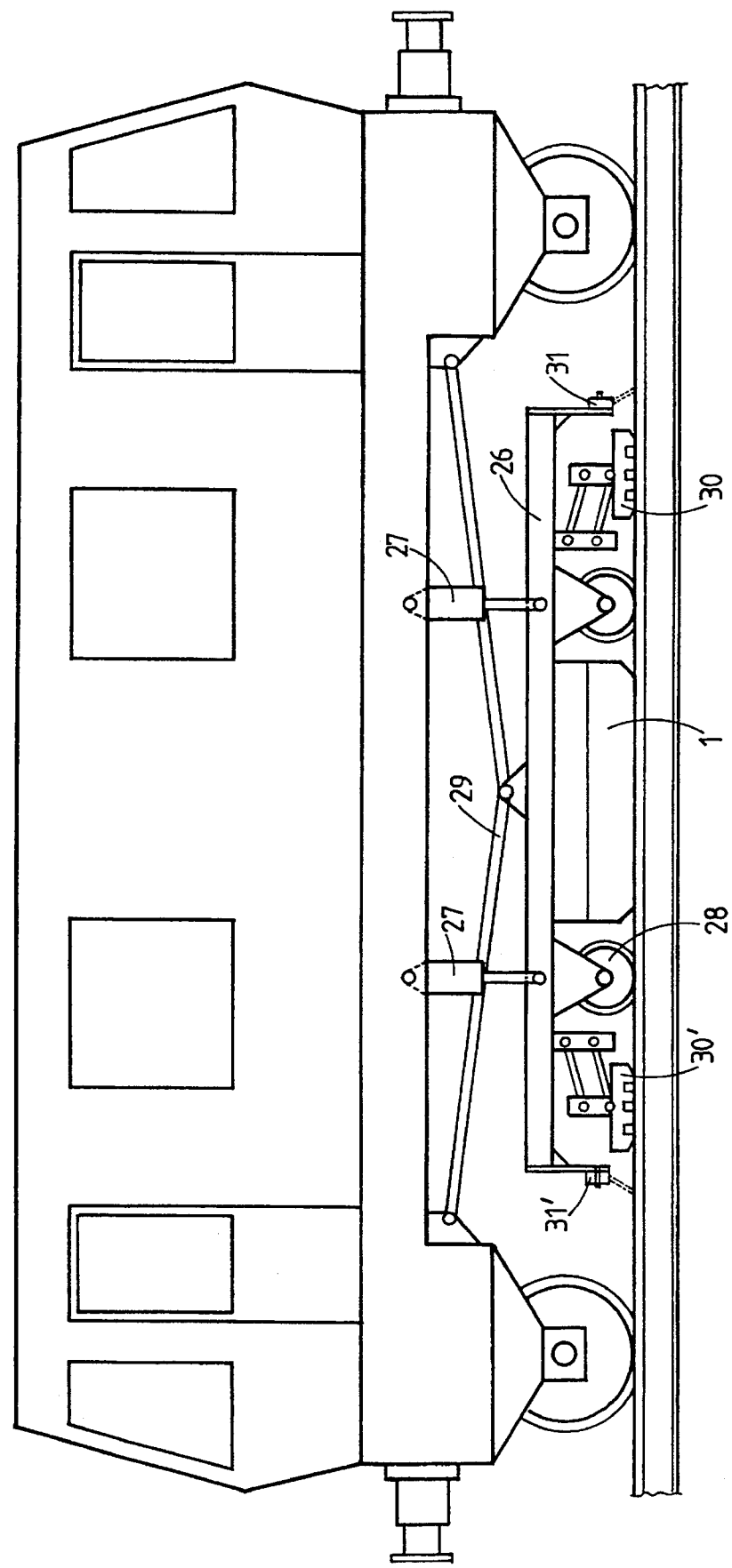
FIG. 7 is a schematic side view of a railway vehicle carrying a measuring device object of the present invention.

FIG. 7 illustrates schematically a railway vehicle carrying a carriage 26 for verifying the railway track which includes an assembly of measuring units 1. This carriage 26 also carries lifting means consisting of the pressure cylinders 27 which make it possible the light running of the installation. This carriage 26 is also connected to the underframe of the railway vehicle via the bars 29 which make it possible to drive the carriage 26 in the direction desired. This measuring carriage 26 can be extended transversally and includes means (not represented) which make it possible to place the side wheels 28 against the inner side of the rail to thus ensure the proper lateral and transverse guiding of the carriage 26 for controlling the tracks. On both sides of the device including the measuring units 1, one can find a device for cleaning the rail 30, 30' which will be described in more detail hereafter. Located in front of the cleaning devices 30, 30' and in the direction of travel, on can see mounted on the carriage 26 the cleaning nozzles 31, 31'. These cleaning nozzles 31, 31' are supplied with water at a pressure of about 100 bars and make it possible to eliminate the debris or dust accumulated on the rail before the passage of the measuring units 1. The nozzles 31, 31' are arranged in such a manner as to spray the track with an angle of about 15° with respect to the vertical axis.

The general circuit for distributing water includes a piston pump capable of delivering the water necessary at a maximum pressure of about 180 bars from a water container situated on the railway vehicle. The water distribution circuit supplies directly a first high pressure circuit which delivers water to the cleaning nozzles 31, 31' and via a pressure reducer a second distribution circuit which supplies the spray nozzles 24, to form the water film on the surface of the rail at a pressure of about 15 bars.

Trials carried out on a railway section have shown that it was not possible to remove completely the residues from the track only by means of the cleaning nozzles 31, 31'. This is why the cleaning devices 30, 30' are arranged behind the cleaning nozzles 31, 31'. These cleaning devices will now be described with reference to FIGS. 8 and 9.

Figure 8:
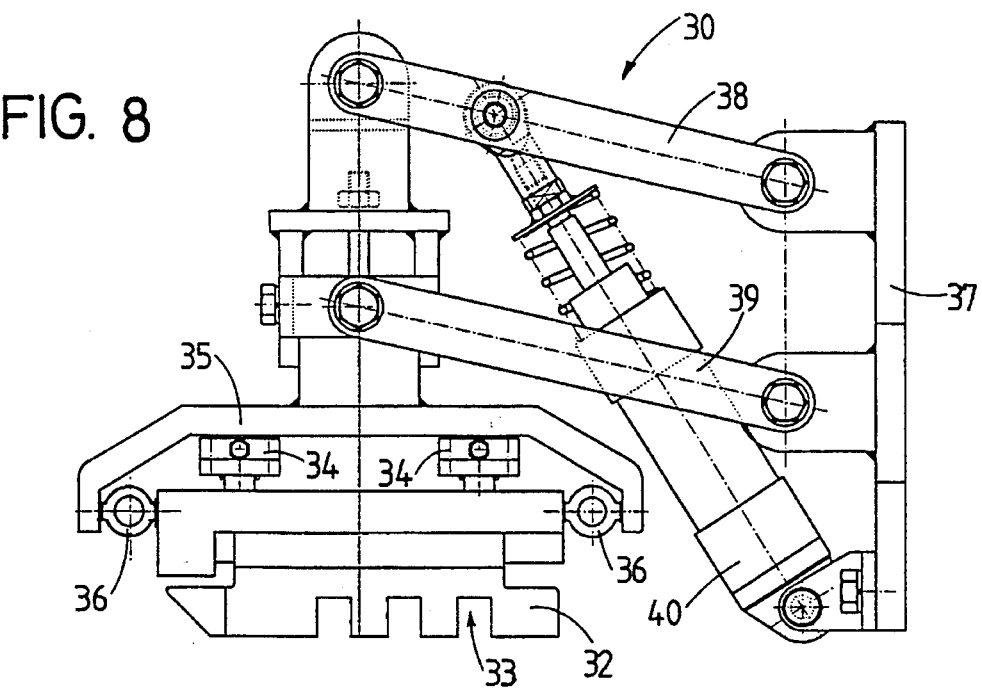
FIG. 8 is a side view of a cleaning device of a railway track, in its lifted position.
Figure 9:
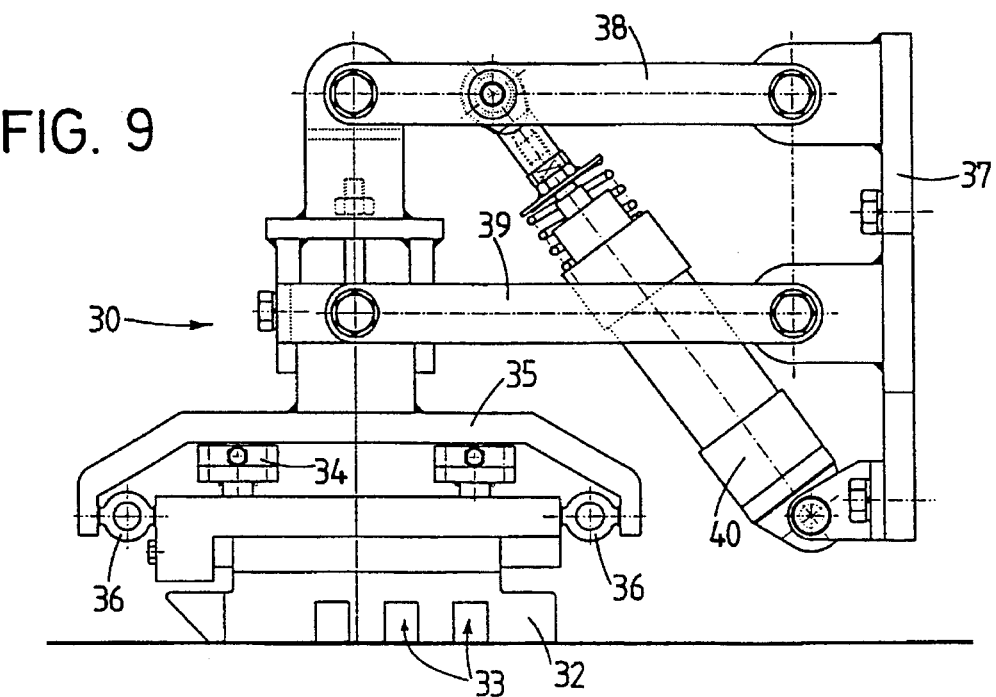
FIG. 9 is a side view of the device illustrated in FIG. 8.

The cleaning device illustrated in FIG. 8 includes a shoe 32 provided with slots 33, mounted via pressure cylinders 34 in a cradle 35. The cylinders 34 make it possible to adjust in a precise manner the force of contact between the shoe 32 and the track. This track 32 is driven in the direction of travel by means of the deformable rings 36 which also function to dampen the vibrations of the shoe 32. The cradle 35 is connected to a fastening plate 37 which is mounted beneath the carriage 26 via two connecting rods 38, 39 pivotally mounted at one of their ends to the upper part of the cradle 35 and by their other end to a fastening plate 37. A pressure cylinder 40, of which the body is connected to the base of the fastening plate 37 and the rod to the upper post 38, makes it possible to lift the whole of the cradle 35 carrying the cleaning shoe 32. It is thus possible to lift, as illustrated in FIG. 9, the entire cleaning device, for example for light running. The shoe 32 scrapes the surface of the track with a determined force, applied by the pressure cylinders 34, which makes it possible to eliminate the debris stuck to the track. The debris are then evacuated outside via the slots 33.

I claim:

1. A measuring device by ultrasound of defects of at least one track of a railway, at least one shoe (1) provided with a bottom plate (10) mounted under a frame (12, 21, 22) and movable vertically with respect to the frame by means (13) enabling lifting and application of the shoe against the track; drive members (14) connecting the frame to the shoe; members (23) for guiding laterally the shoe with respect to the frame, and the shoe (1) including at least two probes (2) mounted slidably in housings of the shoe via a biasing member (9), wherein said biasing member is an adjustable pressure cylinder which is controlled by the speed of travel of the device.

2. A device according to claim 1, wherein said means for lifting and applying the shoe relative to the frame are provided as double action pressure cylinders (13).

3. A device according to claim 1, wherein the drive members (14) re resilient members.

4. A device according to claim 3, wherein the resilient members (14) are formed by deformable rings made of rubber and connecting the frame (12, 21, 22) to the shoe (1).

5. A device according to claim 1, wherein spray nozzles (24) are arranged in the body of the shoe (1) and are supplied with water by conduits (15, 16) to make possible the spraying of a water cone directly on the track.

6. A device according to claim 1, wherein the probes (2) are mounted beneath a support plate (8) forming a stop, the dimensions of which support plate are greater than the dimensions of said housings in which the probes slide.

7. A measuring device by ultrasound of defects of at least one track of a railway, at least one shoe (1) provided with a bottom plate (10) mounted under a frame (12, 21, 22) and movable vertically with respect to the frame by means (13) enabling lifting and application of the shoe against the track; drive members (14) connecting the frame to the shoe; members (23) for guiding laterally the shoe with respect to the frame, and the shoe (1) including at least two probes (2) mounted slidably in housings of the shoe via a biasing member (9), wherein the guiding members for the shoe with respect to the railway track are formed by rods (23) integral with the shoe (1), cooperating with slots situated in vertical posts (21, 22) of the frame (12, 21, 22).

8. A measuring device by ultrasound of defects of at least one track of a railway, at least one shoe (1) provided with a bottom plate (10) mounted under a frame (12, 21, 22) and movable vertically with respect to the frame by means (13) enabling lifting and application of the shoe against the track; drive members (14) connecting the frame to the shoe; members (23) for guiding laterally the shoe with respect to the frame, and the shoe (1) including at least two probes (2) mounted slidably in housings of the shoe via a biasing member (9), wherein conduits for supply (15) and recovery (16) of water are arranged in the body of the shoe (1) and open respectively into water supply chambers located at the front of the probe and into water recovery chambers situated at the back of each one of the probes, the chambers being defined by cutouts (19, 20) provided in said bottom plate (10) of the shoe (1).

9. A device according to claim 8, wherein said cutouts (19, 20) in said bottom plate (10) of the shoe have in a central part of said cutouts, a shape corresponding to the shape of said probes and terminate endwise in triangular cutouts.

10. An installation for measuring defects of at least one track of a railway, comprising a carriage (26) for verifying the railway tracks, which carriage can be moved vertically with respect to an underframe of a vehicle by lifting means (27) and which is pulled along the railway by said underframe, said carriage (26) including at least one measuring unit (1) for measuring by ultrasound said defects, wherein said carriage (26) includes cleaning devices (30, 30') which are located longitudinally on both sides of said at least one measuring unit (1) and which can move vertically with respect to the carriage (26) via lifting members (40).

11. An installation according to claim 10, characterized in that the cleaning devices (30, 30') include a second shoe (32) mounted in a cradle (35), means (34) for applying said second shoe (32) against the track and resilient driving means (36) for said second shoe.

12. An installation according to claim 11, wherein said second shoe (32) includes several transverse slots (33) which make it possible to eliminate debris.

13. An installation according to claim 10, which further includes cleaning nozzles (31, 31') mounted on the carriage (26) for verifying railway tracks respectively at the front and at the back of the cleaning devices (30, 30').

14. An installation according to claim 13, wherein the cleaning nozzles (31, 31') make it possible to project a liquid under a pressure in the order of 100 to 150 bars in the direction of the rail with an acute angle comprised between 15° C. and 30° C. relative to a vertical plane perpendicular to the railway tracks.

15. An installation according to claim 10, wherein a low pressure supply of spray nozzles (24) or a high pressure supply of cleaning nozzles (30, 30') is controlled by the speed of travel of the installation.

* * * * *